(12) United States Patent
Urano et al.

(10) Patent No.: US 9,865,046 B2
(45) Date of Patent: Jan. 9, 2018

(54) DEFECT INSPECTION METHOD AND DEFECT INSPECTION DEVICE

(71) Applicant: HITACHI HIGH-TECHNOLOGIES CORPORATION, Minato-ku, Tokyo (JP)

(72) Inventors: Takahiro Urano, Tokyo (JP); Toshifumi Honda, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 14/758,063

(22) PCT Filed: Dec. 11, 2013

(86) PCT No.: PCT/JP2013/083192
§ 371 (c)(1),
(2) Date: Jun. 26, 2015

(87) PCT Pub. No.: WO2014/103719
PCT Pub. Date: Jul. 3, 2014

(65) Prior Publication Data
US 2015/0356727 A1   Dec. 10, 2015

(30) Foreign Application Priority Data
Dec. 26, 2012  (JP) ................ 2012-282474

(51) Int. Cl.
*G06K 9/00* (2006.01)
*G06T 7/00* (2017.01)
(Continued)

(52) U.S. Cl.
CPC ......... *G06T 7/0008* (2013.01); *G01N 21/956* (2013.01); *G06T 1/0007* (2013.01);
(Continued)

(58) Field of Classification Search
None
See application file for complete search history.

(56) References Cited

U.S. PATENT DOCUMENTS 7,221,992 B2   5/2007   Smith et al.
2002/0027653 A1 *  3/2002   Shibata .............. G01N 21/9501
356/237.3
(Continued)

FOREIGN PATENT DOCUMENTS

JP    2003-83907 A    3/2003
JP    3566589 B2      9/2004
(Continued)

*Primary Examiner* — Ryan P Potts
(74) *Attorney, Agent, or Firm* — Miles & Stockbridge P.C.

(57) ABSTRACT

In order to achieve highly precise alignment of inspection images when integrating a plurality of inspection images having different imaging conditions to improve inspection performance, and in order to achieve highly precise alignment of images acquired at different inspection angles and different polarization states, an inspection device is configured to comprise: an image acquiring unit that acquires image data, under a plurality of imaging conditions, for a sample; a feature extracting unit that extracts at least one feature point; a position correction calculating unit that calculates, on the basis of the feature point, the amount of position correction for the plurality of image data sets; a position correcting unit that corrects the position of the plurality of image data sets with the amount of position correction; and an integrating unit that detects defects by integrating a plurality of data sets for which position correction is done.

6 Claims, 17 Drawing Sheets

(51) Int. Cl.
  *G06T 1/00* (2006.01)
  *G01N 21/956* (2006.01)
  *G06T 7/33* (2017.01)

(52) U.S. Cl.
  CPC .............. *G06T 7/0004* (2013.01); *G06T 7/33* (2017.01); *G06T 2207/10004* (2013.01); *G06T 2207/10056* (2013.01); *G06T 2207/10152* (2013.01); *G06T 2207/30148* (2013.01); *G06T 2207/30244* (2013.01)

(56) References Cited

U.S. PATENT DOCUMENTS

| | | |
|---|---|---|
| 2002/0168787 A1 | 11/2002 | Noguchi et al. |
| 2004/0246476 A1* | 12/2004 | Bevis .................. G01N 21/474 356/237.5 |
| 2005/0033528 A1* | 2/2005 | Toth .................. G01N 21/9501 702/35 |
| 2007/0036422 A1* | 2/2007 | Sakai .............. G01N 21/95607 382/149 |
| 2008/0015802 A1* | 1/2008 | Urano ................ G01N 21/4738 702/81 |
| 2008/0239289 A1 | 10/2008 | Ueno et al. |
| 2008/0285023 A1 | 11/2008 | Tsai et al. |
| 2008/0297783 A1 | 12/2008 | Urano et al. |
| 2009/0180680 A1* | 7/2009 | Satou ...................... G06T 7/001 382/144 |
| 2010/0195896 A1* | 8/2010 | Shibuya ........... G01N 21/95607 382/149 |
| 2011/0133066 A1* | 6/2011 | Nozoe ................... H01J 37/265 250/252.1 |
| 2011/0261190 A1* | 10/2011 | Nakagaki ................ G06T 7/001 348/126 |
| 2011/0311126 A1 | 12/2011 | Sakai et al. |
| 2013/0064442 A1* | 3/2013 | Chang ..................... G06T 7/001 382/149 |
| 2013/0294677 A1 | 11/2013 | Urano et al. |

FOREIGN PATENT DOCUMENTS

| | | |
|---|---|---|
| JP | 2008-268141 A | 11/2008 |
| JP | 2008-268199 A | 11/2008 |
| JP | 2010-175270 A | 8/2010 |
| JP | 2012-112915 A | 6/2012 |

\* cited by examiner

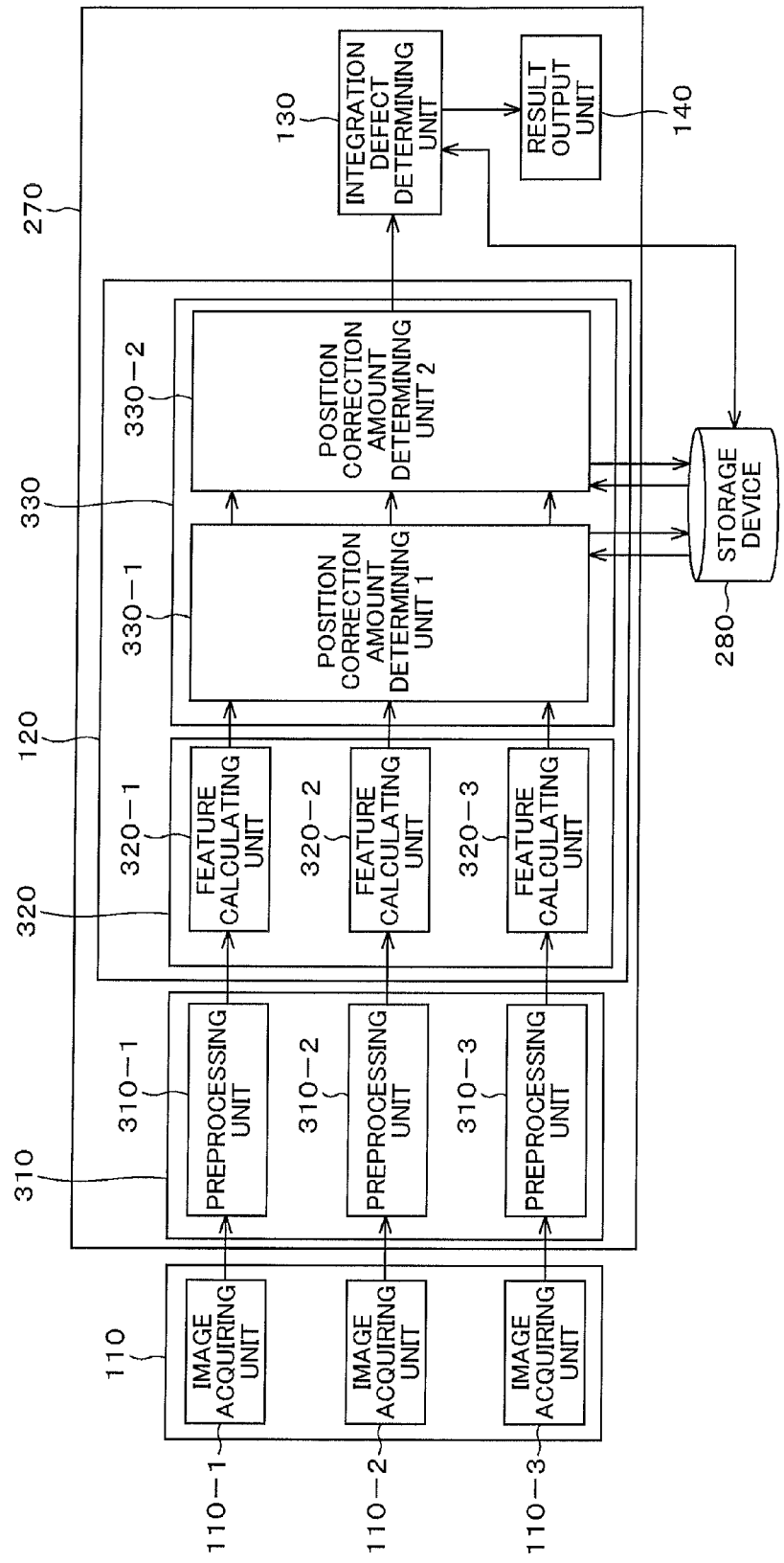

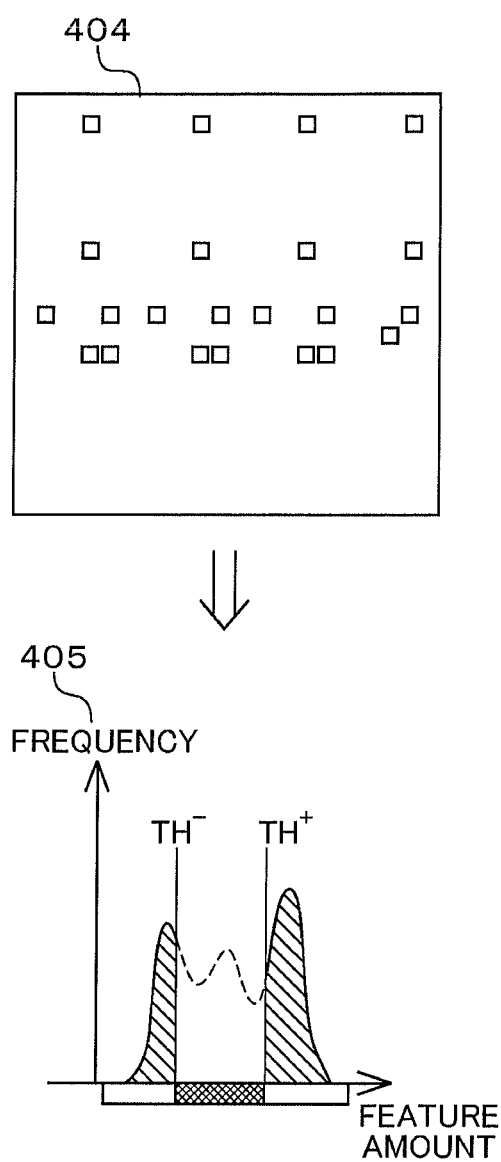

DEFECT INSPECTION METHOD AND DEFECT INSPECTION DEVICE

BACKGROUND

The present invention relates to a defect inspection method and a defect inspection device inspecting a minute defect existing in the surface of a sample with high sensitivity.

Thin film devices such as semiconductor wafers, liquid crystal displays, and hard disk magnetic heads, are manufactured through a number of processes. In manufacturing these thin film devices, an appearance inspection is carried out in each series of processes for improving the yield and achieving stabilization.

Patent Literature 1 (Japanese Patent No. 3566589) discloses a method "which detects a pattern defect or a defect such as foreign substance based on a three-illuminated image and an inspection image that are obtained by using lamp light, laser light, or an electron beam, for corresponding areas in two patterns formed to have the same shape in the appearance inspection."

As a technique for improving the inspection sensitivity, Patent Literature 2 (U.S. Pat. No. 7,221,992) and Patent Literature 3 (U.S. Patent Publication No. 2008/285023) disclose "a method which simultaneously detects images under a plurality of different optical conditions, compares the brightness of them with a three-illuminated image for each of the conditions, and integrates the comparison values to determine a defect and a noise."

On the other hand, in order to integrate images of a plurality of optical conditions, the images have to be aligned with one another. Patent Literature 4 (Japanese Patent Application Laid-Open No. 2008-268199) discloses "a method which calculates the position deviation amounts of the respective images in advance by using a standard sample or the like and uses those position deviation amounts for alignment." Patent Literature 5 (Japanese Patent Application Laid-Open No. 2003-83907) discloses a method for correcting color unevenness, position deviation, and image distortion in inspection object images.

CITATION LIST

Patent Literature

Patent Literature 1: Japanese Patent No. 3566589
Patent Literature 2: U.S. Pat. No. 7,221,992
Patent Literature 3: U.S. Patent Publication No. 2008/285023
Patent Literature 4: Japanese Patent Application Laid-Open No. 2008-268199
Patent Literature 5: Japanese Patent Application Laid-Open No. 2003-83907

SUMMARY OF THE INVENTION

In order to integrate a plurality of inspection images having different imaging conditions, alignment of the respective inspection images is required. In order to improve the inspection performance, the inspection images have to be aligned with each other highly precisely. In the alignment method disclosed in Patent Literature 4, the alignment is performed by using a standard sample that is not an object of inspection and therefore highly precise alignment between the images to be inspected is difficult. Moreover, images acquired at different detection angles or in different polarization states may be images having different profiles, even if the background patterns are the same. Thus, in the position determination method in which the residual between the images is the minimum as disclosed in Patent Literature 5, highly precise alignment is difficult.

In order to solve the aforementioned problems, according to the present invention, a defect inspection method is provided which includes: imaging an inspection object under different conditions to acquire a plurality of images having different imaging conditions for the same portion on the inspection object; extracting a feature point in the acquired images having the different imaging conditions and calculating position correction amounts for matching positions of the feature point in each of the images; correcting positions of the images based on the calculated position correction amounts; calculating feature amounts for the images for which the positions thereof have been corrected; and extracting a defect candidate of the inspection object based on the calculated feature amounts.

Also, in order to solve the aforementioned problem, according to the present invention, a defect inspection device is provided which includes: an image acquiring unit configured to image an inspection object under different conditions to acquire a plurality of images having different imaging conditions for the same portion on the inspection object; a feature point extracting unit configured to extract a feature point in the plurality of images having the different imaging conditions acquired by the image acquiring unit; a position correction amount calculating unit configured to calculate position correction amounts for matching positions of the feature point extracted by the feature point extracting unit in each of the plurality of images having the different imaging conditions acquired by the image acquiring unit; an image position correcting unit configured to correct positions of the plurality of images based on the position correction amounts calculated by the position correction amount calculating unit; a feature amount calculating unit configured to calculate feature amounts for the plurality of images the positions of which have been corrected by the image position correcting unit; and a defect candidate extracting unit configured to extract a defect candidate of the inspection object based on the feature amounts calculated by the feature amount calculating unit.

According to the invention disclosed in the present application, a defect inspection method and a defect inspection device can be provided which inspect a minute defect existing in the surface of a sample with high sensitivity.

BRIEF DESCRIPTION OF THE DRAWINGS

FIG. 3 is a block diagram showing a structure of a position correction amount calculating unit of the defect inspection device according to the first embodiment of the present invention.

FIG. 4B shows an image obtained by quantizing the feature amount image created from the image of the inspection sample acquired by imaging in the defect inspection device according to the first embodiment of the present invention, and a histogram showing the feature amount distribution therein.

DESCRIPTION OF EMBODIMENTS

Figure 1:
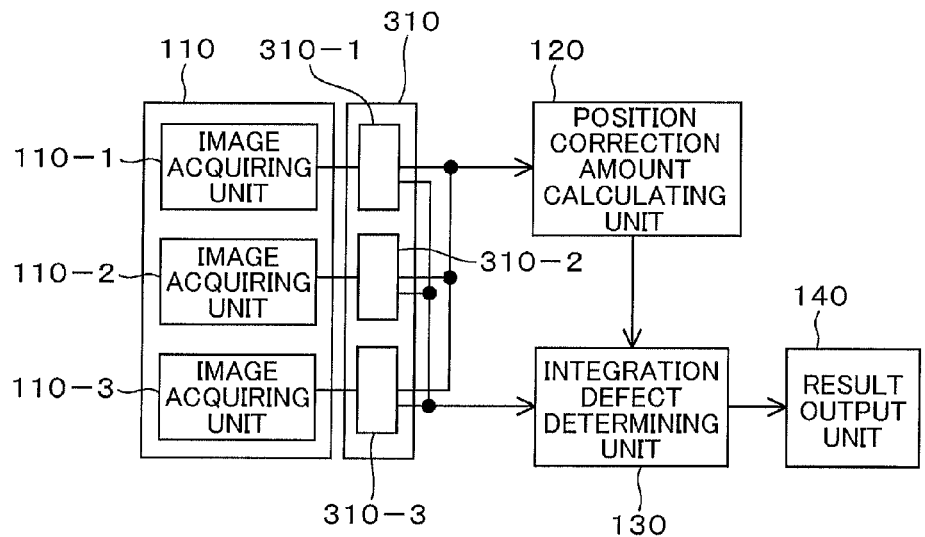
FIG. 1 is a block diagram showing a schematic structure of a defect inspection device according to a first embodiment of the present invention.

One of features of the present invention is that, in a case where a defect on a sample is detected from a plurality of images acquired by imaging the same portion of the sample under a plurality of imaging conditions, position deviations between the plurality of images having the different imaging conditions are precisely corrected and then a defect candidate is detected from feature amounts in the respective images for which the position deviations have been corrected, thereby information on the defect detected from the respective images can be precisely integrated.

Embodiments of the present invention are described below in detail based on the drawings. Please note that throughout all the drawings for explaining the respective embodiments the same components are labeled with the same reference numerals in principle and the redundant description thereof is omitted.

First Embodiment

In the following description, the first embodiment of a defect inspection technique (defect inspection method and defect inspection device) according to the present invention is described in detail, referring to FIGS. 1 to 9.

As the first embodiment of a pattern inspection technique of the present invention, a defect inspection device and a defect inspection method for a semiconductor wafer as an object, utilizing dark field illumination, are described.

FIG. 1 shows an exemplary structure of the defect inspection device of this embodiment. The defect inspection device according to this embodiment is configured to include an image acquiring unit 110 formed by image acquiring units 110-1 to 110-3, a preprocessing unit 310 formed by preprocessing units 310-1 to 310-3, a position correction amount calculating unit 120, a defect determining unit 130, and a result output unit 140.

The image acquiring unit 110 images a sample under a plurality of imaging conditions and outputs the acquired images to the position correction amount calculating unit 120 and the defect determining unit 130. The preprocessing unit 310 performs shading correction and dark level correction, for example, for the images acquired by the image acquiring unit 110. The position correction amount calculating unit 120 performs position matching for the images of the respective conditions which have been acquired by the image acquiring units 110-1, 110-2, and 110-3 of the image acquiring unit 110 and have been subjected to preprocessing such as shading correction and dark level correction by the preprocessing units 310-1, 310-2, and 310-3 of the preprocessing unit 310, and calculates the position correction amounts and outputs them to the defect determining unit 130. The defect determining unit 130 performs position correction for the images of the respective conditions based on the calculated position correction amounts, then performs defect determination using the acquired images of the respective conditions the positions of which have been corrected, and outputs the result to the result output unit 140.

In FIG. 1, the structure in which the image acquiring unit 110 includes three image acquiring units 110-1, 110-2, and 110-3 respectively provided for different image acquiring conditions is shown, where the different image acquiring conditions are acquisition of inspection images under different conditions of illumination or detection for a sample or with different detection sensitivity, for example. Moreover, the images of the plurality of conditions are not limited to be acquired at the same time. The images may be acquired by performing scanning a plurality of times or performing scanning in different directions.

Figure 2:
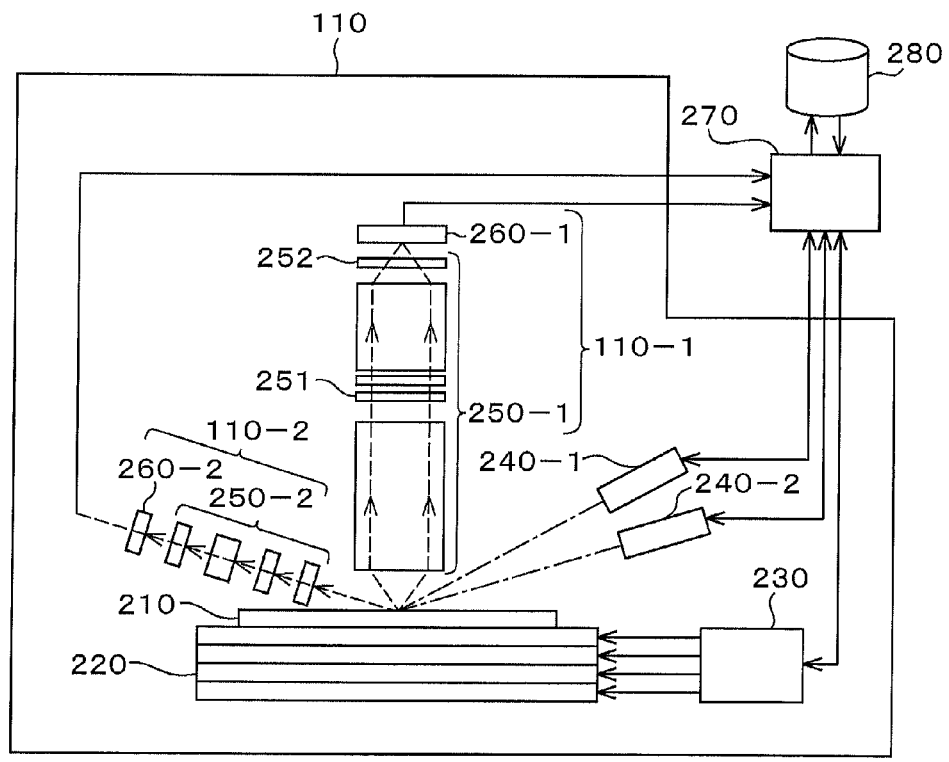
FIG. 2 is a block diagram showing a schematic structure of an image acquiring unit of the defect inspection device according to the first embodiment of the present invention.

FIG. 2 is a diagram showing an exemplary structure of the defect inspection device utilizing dark field illumination according to the first embodiment. The defect inspection device utilizing dark field illumination includes a stage 220, a mechanical controller 230, two illumination optical systems (illumination units) 240-1 and 240-2, detection optical systems (upward detector system) 250-1 and (oblique detector system) 250-2, image sensors 260-1 and 260-2, an image processor and controller unit 270, and a storage device 280. The detection optical system includes a spatial frequency filter 251 and an analyzer 252. A sample 210 is an object to be inspected such as a semiconductor wafer. The stage 220 can be moved and rotated (θ) in the XY plane and can be moved in the Z direction with the sample 210 mounted thereon. The mechanical controller 230 is a controller which drives the stage 220.

The combination of the detection optical system (upward detector system) 250-1 and the image sensor 260-1 corresponds to the image acquiring unit 110-1 in FIG. 1, for example, and the combination of the detection optical system (oblique detector system) 250-2 and the image sensor 260-2 corresponds to the image acquiring unit 110-2 in FIG. 1, for example. In the structure shown in FIG. 2, the structure corresponding to the image acquiring unit 110-3 of the image acquiring unit 110 in FIG. 1 is omitted. The image processor and controller unit 270 corresponds to the structure including the preprocessing units 310-1 and 310-2 of the preprocessing unit 310, the position correction amount calculating unit 120, the integrated defect determining unit 130, and the result output unit 140 in the structure shown in FIG. 1.

In the structure shown in FIG. 2, light from the illumination units 240-1 and 240-2 is irradiated onto the sample 210, the scattered light from the sample 210 is converged by the upward detector system 250-1 and the oblique detector system 250-2, and the converged optical image is received by the respective image sensors 260-1 and 260-2 to be converted into image signals. During this, the sample 210 is mounted on the stage 220 movable in X-Y-Z-θ directions, and scattered light from foreign substance on the sample 210 is detected while the stage 220 is being moved in the horizontal direction in the X-Y plane. In this manner, the detection result is obtained as a two-dimensional image.

As illumination light sources used for the illumination units 240-1 and 240-2, laser or lamp may be used. The light from each of the light sources of the illumination units 240-1 and 240-2 may have a short wavelength or may be broadband wavelength light (white light). In a case of using short-wavelength light, light having a wavelength in an ultraviolet band (ultra violet light: UV light) can be used for increasing the resolution of an image to be detected (for detecting a minute defect). In a case of using laser that is single-wavelength laser as the light source, a component for reducing coherence can be provided in each of the illumination units 240-1 and 240-2.

Moreover, it is possible to acquire a two-dimensional image at a relatively high speed with high sensitivity by using time delay integration image sensors (TDI image sensors) each of which is formed by a plurality of one-dimensional image sensors arranged two-dimensionally, as the image sensors 260-1 and 260-2, transferring the signal detected by each one-dimensional image sensor in synchronization with the movement of the stage 220 to the one-dimensional image sensor in the next stage, and adding the signals. The use of a parallel-output type sensor having a plurality of output taps as this TDI image sensor enables parallel processing of the outputs of the sensor, thus enabling detection at a higher speed. In addition, when a backside illumination type sensor is used for the image sensor 260, the detection efficiency can be increased as compared with a case of using a conventional front-side illumination type sensor.

The sensor output signals output from the image sensors 260-1 and 260-2 are input to the image processor and controller unit 270. The image processor and controller unit 270 includes the preprocessing units 310-1 to 310-3, the position correction amount calculating unit 120, the integrated defect determining unit 130, and the result output unit 140 as shown in FIG. 1, creates image data from the sensor output signals output from the image sensors 260-1 and 260-2, and performs processing which processes the image data to detect a defect. In this case, it is also possible to store the image data in the storage device 280, and output the stored image data to the position correction amount calculating unit 120 and the defect determining unit 130.

FIG. 3 is a diagram showing the structure of the position correction amount calculating unit 120 of the image processor and controller unit 270 which receives and processes the signals from the preprocessing unit 310 in this embodiment. The position correction amount calculating unit 120 is configured to include a feature calculating unit 320, a position correction determining unit 330-1, and a position correction determining unit 330-2. The signals input to the position correction amount calculating unit 120 are the signals from the preprocessing unit 310 which receives the sensor output signals acquired by a plurality of image acquiring units 110, creates images, and performs processing such as shading correction and dark level correction.

In the image processor and controller unit 270 to which the signals preprocessed in the preprocessing unit 310 are input, the images received from the preprocessing units 310-1 to 310-3 of the preprocessing unit 310 are respectively processed by feature calculating units 320-1 to 320-3 of the feature amount calculating unit 320 first, so that feature distributions in the images are calculated. The feature extracted here is a feature amount image having one or more values for each pixel, a feature point having information on a coordinate on the sample, or a weighed feature point at which the aforementioned feature point has a feature amount of a real number value or an attribute of a discrete value, for example.

Examples of the aforementioned feature are described below. The feature extracted in the feature amount calculating unit 320 is (1) a feature such as a signal strength of each point in an image, a ratio of signal strength to background noise (SNR), an edge strength, or a pattern density, (2) a feature point such as a point detected as a defect candidate, an edge corner, the center of gravity of a pattern, or a point obtained by quantizing the aforementioned feature amount, and (3) a weighed feature point obtained by adding, to position information of the point detected as the defect candidate or the point extracted as the edge, the feature amount such as the signal strength, the defect size, the ratio of signal strength to background noise (SNR), or the direction or strength value of the edge, a value obtained by quantizing the signal strength or the edge direction, or an attribute such as a defect type.

In a case where the relation between an optical condition and characteristics of scattered light obtained from a wiring pattern or a defect is known in the defect inspection device of this embodiment, the feature amount corresponding thereto may be calculated. Moreover, a feature amount robust to a change in the characteristics of the scattered light, e.g., the center of gravity of a given area of the brightness of the wiring pattern, a feature amount considering the spreading the detected scattered light, or the like may be used. The feature calculating unit 320 can output a plurality of types of features simultaneously.

Moreover, at least one type of image obtained by changing the resolution of the image acquired from the image acquiring unit 110 may be calculated in advance in the preprocessing unit 310, and feature calculation may be performed for the image of each resolution by the feature calculating unit 320. By performing feature calculation for the images having the different resolutions, features of patterns having different frequency characteristics can be obtained.

Furthermore, image acquisition may be performed in the image acquiring unit 110 so that the image contains an alignment mark on the sample. The feature calculating unit 320 can perform feature calculation for the alignment mark, too, to calculate a feature amount image or a feature point. Since the position of the alignment mark on the sample is known, it is also possible to give the attribute for enabling the alignment mark to be recognized, to the feature calculated from the position of the alignment mark.

Figure 4A:
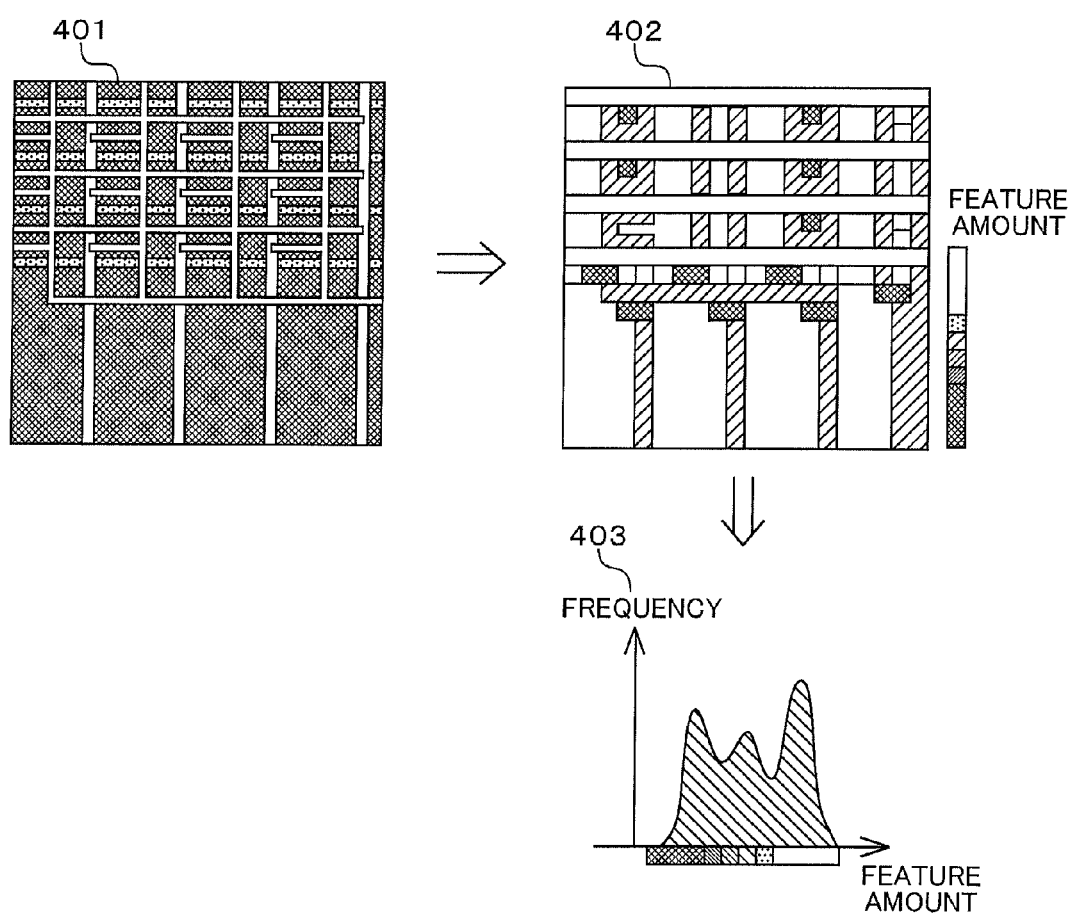
FIG. 4A shows an image of a sample to be inspected acquired by imaging in the defect inspection device according to the first embodiment of the present invention, a feature amount image obtained by extracting the edge strength of the background pattern of the above image as a feature amount, and a histogram of the feature amount of the image.
Figure 4C:
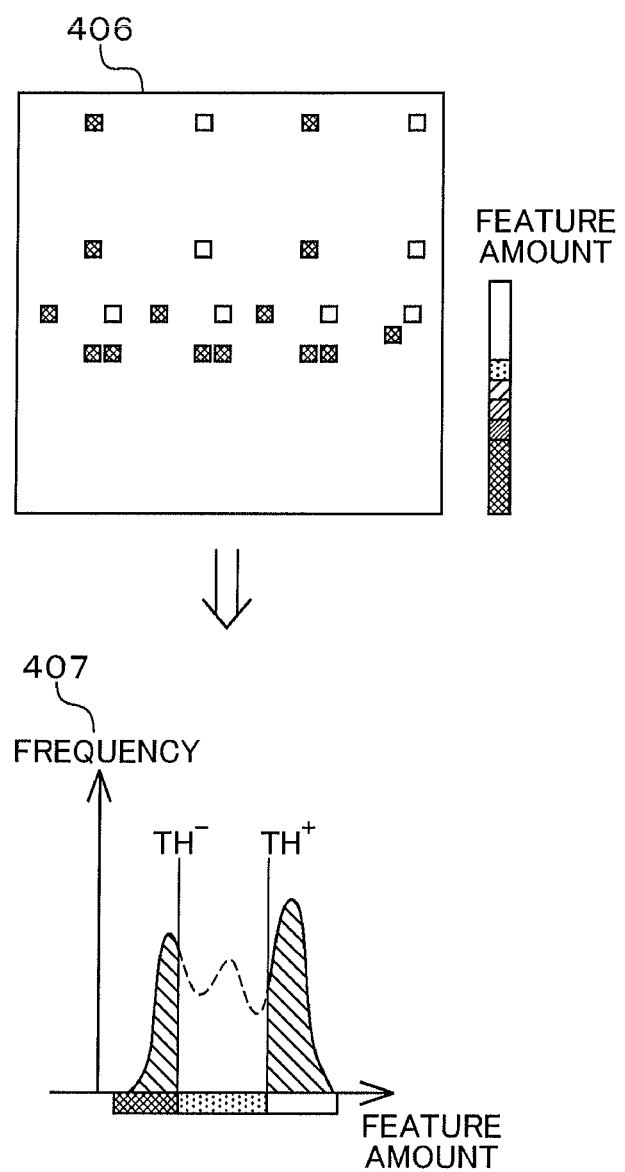
FIG. 4C shows an image showing weighted feature points obtained by weighing feature points in the feature amount image created from the image of the inspection sample acquired by imaging in the defect inspection device according to the first embodiment of the present invention, and a histogram showing the feature amount distribution therein.

FIGS. 4A to 4C are diagrams showing an example of the feature amount image, the feature amount, and the weighed feature amount. 401 in FIG. 4A denotes an image captured by the image acquiring unit 110 and formed by the preprocessing unit 310. A feature amount image obtained by extracting the edge strength of the background pattern from the acquired image 401 as a feature amount is denoted as 402, and a histogram in which the horizontal axis represents the feature amount extracted from the feature amount image 402 and the vertical axis represents the frequency of the extracted feature amount is denoted as 403. An image 404 in FIG. 4B shows feature points obtained by quantizing the feature amount image 402 in FIG. 4A. A distribution after threshold values (TH− and TH+) are set for the histogram 403 and quantization is performed is shown in 405. Moreover, an image 406 in FIG. 4C shows weighed feature points obtained by giving the respective feature points in the feature amount image 402 in FIG. 4A the feature amounts, and a histogram of the respective feature amounts is shown in 407.

The position correction amount determining unit 330 determines the position correction amounts for the respective images acquired by the image acquiring unit 110 from the feature amount images, the feature points, or the weighed feature points received from the respective feature calculating units 320-1, 320-2, and 320-3 of the feature amount calculating unit 320, or from the combination of them. By using the position correction amounts it is performed a position correction for the feature extracted from the image of the condition as the object with respect to the feature extracted from an image of a reference condition which is determined in advance, thereby performing position correction between the images. The reference condition and the correction target condition may be a given combination, or may be a given method, for example, in which the condition for which the number of the extracted feature points is the maximum is used as the reference condition while other conditions are used as the correction target conditions. Moreover, a combination effective to calculation of the position correction amounts may be determined in advance from the direction of the wiring pattern on the sample, the direction in which the sample is scanned, or the relation of the polarization states of the illuminations.

Moreover, in a case where it is known in advance that images of a plurality of conditions acquired by the same scanning have small position deviation amounts in the defect inspection device of the present embodiment, the images acquired by the same scanning can be combined with priority. For example, factors of the position deviation caused in the same scanning include vibrations of the image sensors 260-1, 260-2 or the stage 220, and the magnification or the deviation of the attachment position of each of the image sensors 260-1 and 260-2. For those factors, the deviation amount is small or the direction or the amount of deviation can be obtained in advance, and therefore calculation of the position correction amounts can be performed easily. On the other hand, in a case where position correction with respect to data obtained by scanning after the sample has been inspected once and then rotated at 90 degrees or 180 degrees, the relative positions of the stage 220 and the sample 210, the scanning speed of the stage 220, the error in the scanning direction, and the like are different. Thus, for those, the position deviation amount is large and it is impossible to obtain the deviation amount in advance. Therefore, by performing position correction between the images acquired by the same scanning with priority, it is possible to precisely calculate the position correction amounts.

Moreover, a plurality of position correction amount determining units 330 may be provided. In this case, the position correction amounts can be determined by different features in each of the plurality of position correction amount determining units 330-1 and 330-2. For example, the position correction amount determining unit 330-1 calculates the position correction amounts by using a feature that is not suitable for fine alignment but hardly causes a large error, such as an edge corner, and thereafter the position correction amount determining unit 330-2 performs fine alignment by a feature amount image such as the signal strength. By calculating the position correction amounts in a plurality of position correction amount determining units in this manner, calculation of erroneous position correction amounts can be reduced, and a calculation time related to position correction can be also reduced. Furthermore, FIG. 3 shows an example configured by two position correction amount determining units 330-1 and 330-2, but the structure is not limited thereto. It is enough that at least one position correction amount determining unit is provided.

Figure 5A:
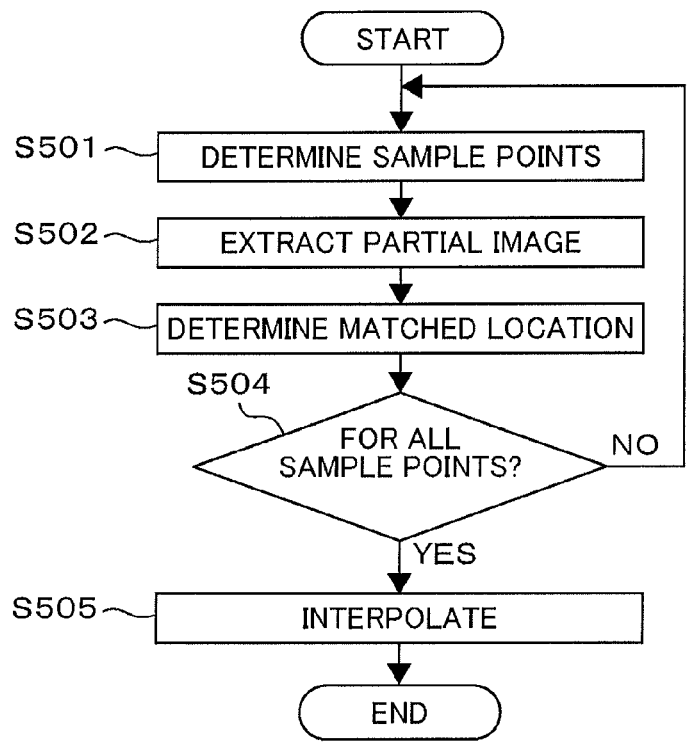
FIG. 5A is a flowchart showing a flow of processing for calculating a deviation amount in a case where a position correction amount determining unit receives the feature amount image in the defect inspection device according to the first embodiment of the present invention.

As an exemplary deviation amount calculation method in a case where the position correction amount determining unit 330 receives the feature amount images, the following method is described referring to the flowchart in FIG. 5A.
(1) Sample points, for each of which the position correction amount is calculated from the feature amount image to be corrected, are determined (S501).
(2) A partial image in a fixed range around the sample point is extracted from the feature amount image to be corrected (S502).
(3) A portion of a feature amount image of a reference image, which is most closely matched by the above partial image, is determined (S503).

(4) (2) and (3) are repeated for all the sample points (S504).
(5) For portions other than the sample points, interpolation is performed based on the deviation amounts at the near sample points (S505). The sample points in the above (S501) may be set for all pixels in the feature amount image to be corrected, or may be set with a constant sample interval, or may be set to feature points extracted from the image to be corrected.

Figure 5B:
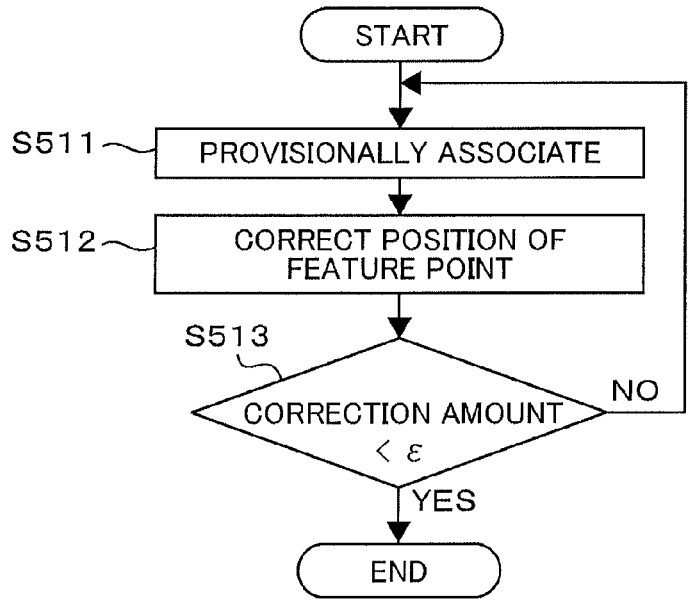
FIG. 5B is a flowchart showing a flow of processing for calculating the deviation amount in a case where the position correction amount determining unit receives position information of the feature point in the defect inspection device according to the first embodiment of the present invention.

On the other hand, the following method is described based on the flowchart of FIG. 5B, as an exemplary method for calculating the deviation amount in a case where the position correction amount determining unit 330 receives position information of the feature points from the feature amount calculating unit 320.
(1) The closest one of reference feature points from each feature point in the correction object is determined to be provisionally associated with each other (S511).
(2) The positions of the feature points in the correction object are corrected so that the sum of the distances between the provisionally associated feature points is minimized (S512).
(3) The above (1) and (2) are repeated until the position correction amount is converged (S513).

In a case where the position correction amount determining unit 330 receives not only the position information of the feature points but also information on the weighed feature points, the feature points for which provisional association is performed in the above (S511) may be determined based on not only the distance between the feature points but also the distances weighed with the feature amounts and/or the attributes. Moreover, in calculation of the distance between the feature points in (S512), the weighed distance may be calculated based on the weights of the respective feature points. Furthermore, only the feature point having a specific feature amount or attribute may be used for position correction. For example, an attribute may be given for every fixed defect size and the position correction amount may be calculated for each attribute.

The position correction amount determining unit 330 can input the position correction amounts that are determined in advance from the storage device 280 thereto. Also it is possible to determine the position correction amounts by the position correction amount determining unit 330, after the position deviations are corrected in advance based on the predetermined position correction amounts. Moreover, it is possible to determine a combination of features which is effective to alignment in advance from a plurality of features output from the feature calculating unit 320, and store it in the storage device 280, and perform correction of the position deviation amounts with the stored combination of features. Calculation of the position correction amounts may be performed for a template set at a given location on a wafer. The template can be set based on data stored in the storage device 280, and may be at a location of a specific pattern extracted from the image data or a location specified by a user in advance. By calculating the position correction amounts from only template, the calculation cost required for calculation of the position correction amounts can be reduced, and the pattern that may easily cause an error can be removed so that calculation of the robust position correction amounts is possible.

Figure 6A:
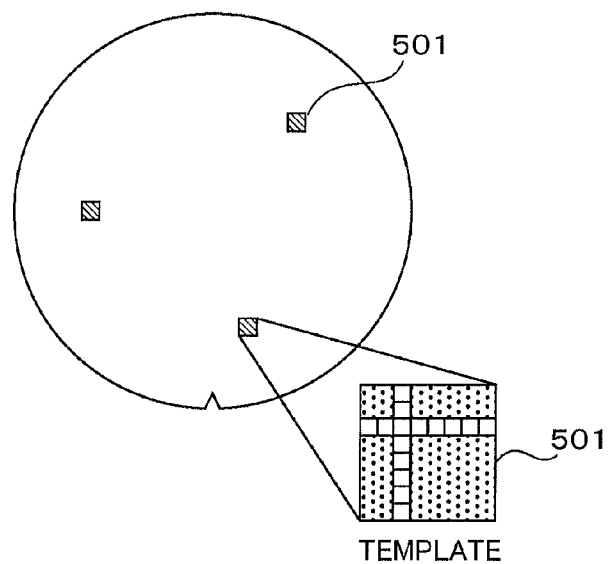
FIG. 6A is a diagram showing an exemplary template using a die as a unit, set in the position correction amount determining unit in the defect inspection device according to the first embodiment of the present invention.
Figure 6B:
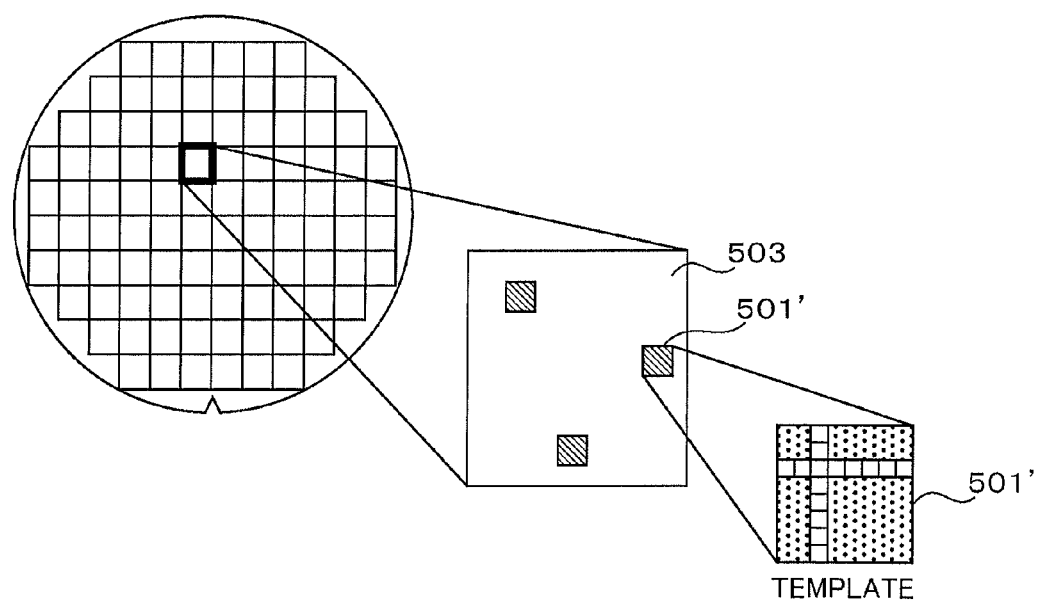
FIG. 6B is a diagram showing an exemplary template using a pattern in a die as a unit, set in the position correction amount determining unit in the defect inspection device according to the first embodiment of the present invention.

FIGS. 6A and 6B are diagrams showing exemplary templates set in the position correction amount determining unit 330. As shown in FIG. 6A, at least one (three in the case of FIG. 6A) template 501 may be set at a given location on a wafer 500 by the position correction amount determining unit 330, so that calculation of the position correction amounts is performed for the template 501. Alternatively, as shown in FIG. 6B, a template 501' (three templates in the case of FIG. 6B) may be set at the same location in each die 503 on the wafer 500.

Figure 7:
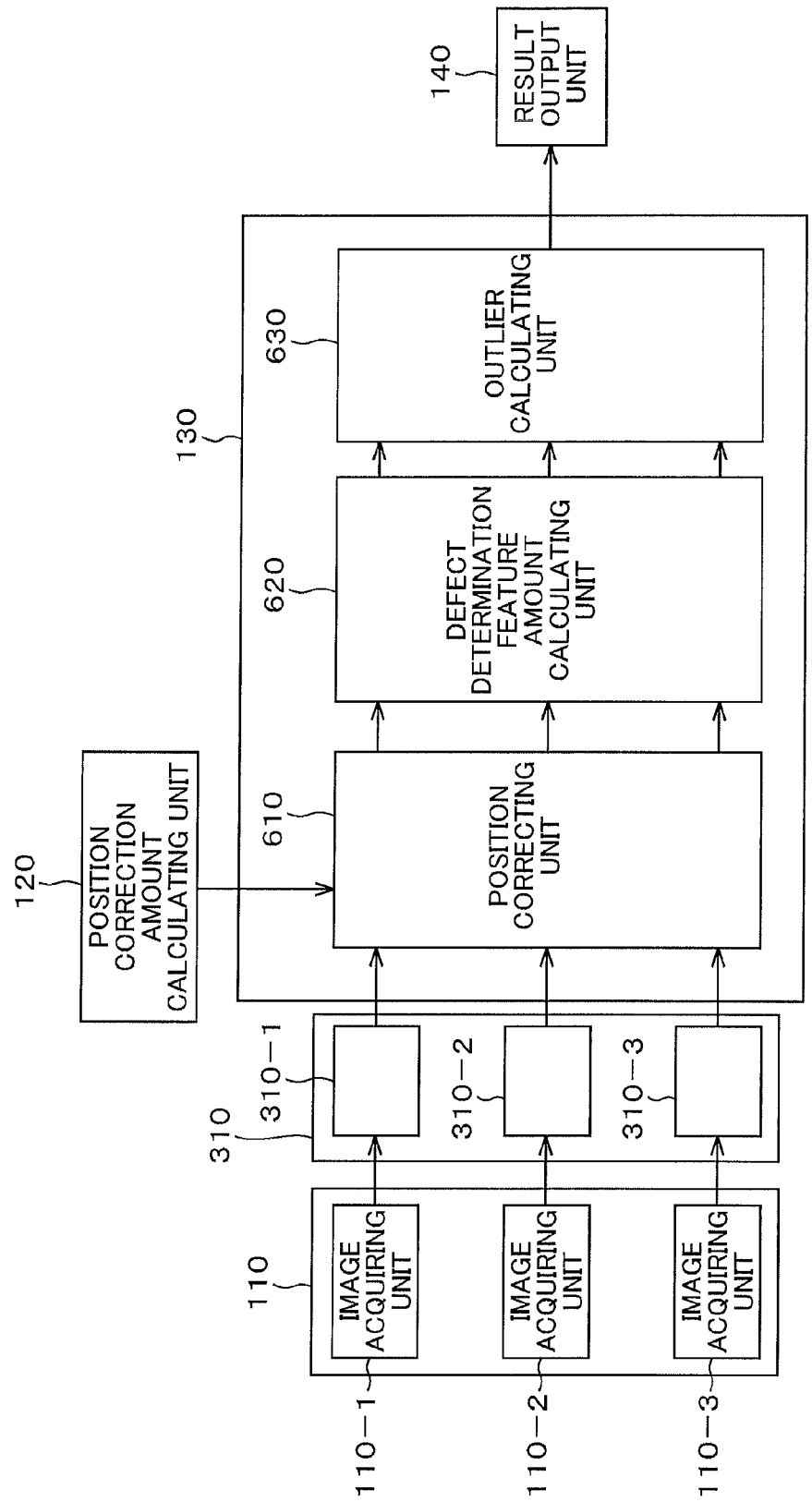
FIG. 7 is a block diagram showing a structure of a defect determining unit in the defect inspection device according to the first embodiment of the present invention.

FIG. 7 is a diagram showing an exemplary structure of the integrated defect determining unit 130 of the defect inspection device according to this embodiment. A defect candidate detecting unit 330 of the integrated defect determining unit 130 includes a position correcting unit 610, a defect determination feature amount calculating unit 620, and an outlier calculating unit 630.

The position correcting unit 610 corrects the positions between the images acquired by the image acquiring units 110-1, 110-2, and 110-3 based on the deviation correction amounts of the respective images calculated by the position correction amount calculating unit 120.

The defect determination feature amount calculating unit 620 extracts at least one type of feature amount for each pixel of the image obtained by imaging by each image acquiring unit 110-1, 110-2, or 110-3 and then subjected to position correction in the position correcting unit 610. The feature amount calculated here is a difference value between pixel values located at corresponding positions in one of a plurality of dies formed on the wafer, which is an inspection object, and in another one adjacent to the inspection object die, for example. Alternatively, the pixel value itself may be used.

The outlier calculating unit 630 outputs a pixel at a separated position in a feature amount space formed by the feature amounts calculated by the defect determination feature amount calculating unit 620, as a defect candidate. The outlier calculating unit 630 may perform normalization of the feature amounts based on variations of the respective defect candidates. As a reference for determining the defect candidate, a variation of data points in the feature amount space, the distance of the data point from the center of gravity, and the like can be used.

Information on the defect candidate output from the outlier calculating unit 630 is displayed on the display screen of the result output unit 140 as a wafer defect candidate map.

Figure 8A:
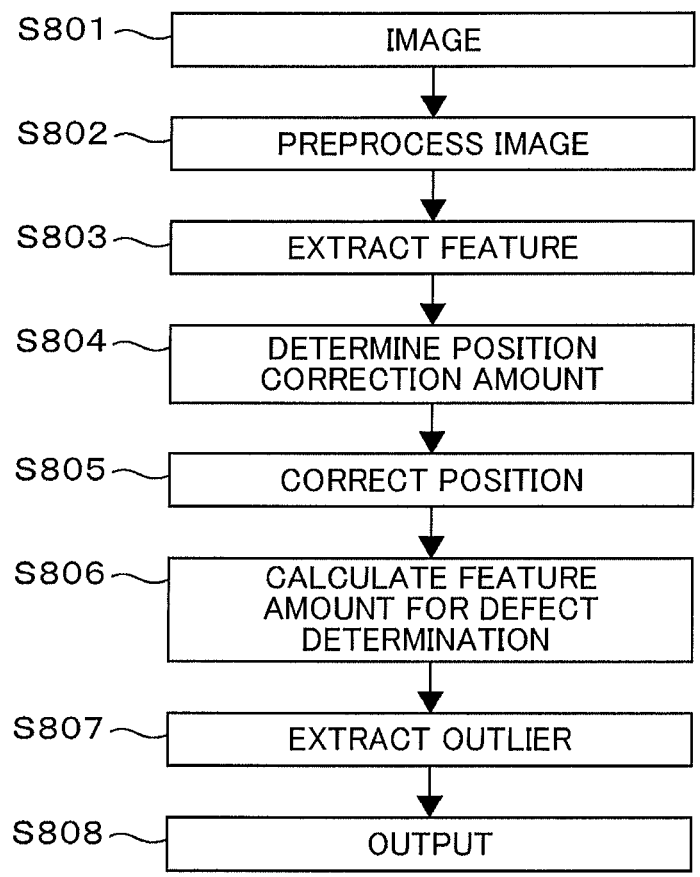
FIG. 8A is a flowchart showing a flow of processing of a defect inspection method according to the first embodiment of the present invention.

FIG. 8A shows the flow of the aforementioned defect candidate extraction in this embodiment.

First, the same position on a sample is imaged by the image acquiring unit 110 under a plurality of different conditions in which the sample illumination direction, the detection direction or the like is different (S801). A plurality of imaging signals of the same position on the sample acquired under those imaging conditions are input to the image processor and controller unit 270. Then, the imaging signals for which the imaging conditions are different, input from the image acquiring unit 110, are processed in the preprocessing unit 310 of the image processor and controller unit 270 to create a plurality of images. The thus created images are subjected to preprocessing such as shading correction and dark level correction (S802).

The images subjected to preprocessing are input to the position correction amount calculating unit 120, and in the feature amount calculating unit 320 the distribution of the feature points on the image is calculated and the feature points are extracted (S803). Then, based on position information of the extracted feature points, the position deviation correction amounts between the images, which are for superimposing the images of the same location on the sample, are calculated in the position correction amount determining unit 330 (S804). The information on the thus calculated position deviation correction amounts is input to the integrated defect determining unit 130.

The position correcting unit 610 of the integrated defect determining unit 130 performs position correction between the preprocessed images of the same portion on the sample input from the preprocessing unit 310, by using the information on the position deviation correction amounts input from the position correction amount determining unit 330 (S805). Then, for the images subjected to this position correction, the feature amounts are calculated by the defect determination feature amount calculating unit 620 (S806). The calculated feature amounts are plotted in a feature amount space by the outlier calculating unit 630 so that an outlier in this feature amount space is extracted as a defect candidate (S807). The information on the extracted defect candidate is sent to the result output unit 140 to be output on the screen as the defect map on the wafer (S808).

Figure 8B:
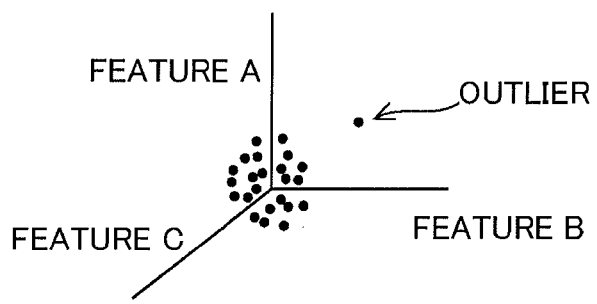
FIG. 8B is a three-dimensional graph showing a state in which extracted feature amounts are plotted in a feature amount space in the defect inspection method according to the first embodiment of the present invention.

FIG. 8B shows a state in which the feature amounts calculated in S806 are plotted in the feature amount space (an example of a three-dimensional space is shown in the case of FIG. 8B). There is a plotted point on the upper right of a group of plotted feature amounts which is separated from the group (labeled with "OUTLIER" in the drawing). The point having such a feature is extracted as the defect candidate in the step of S807.

Figure 9:
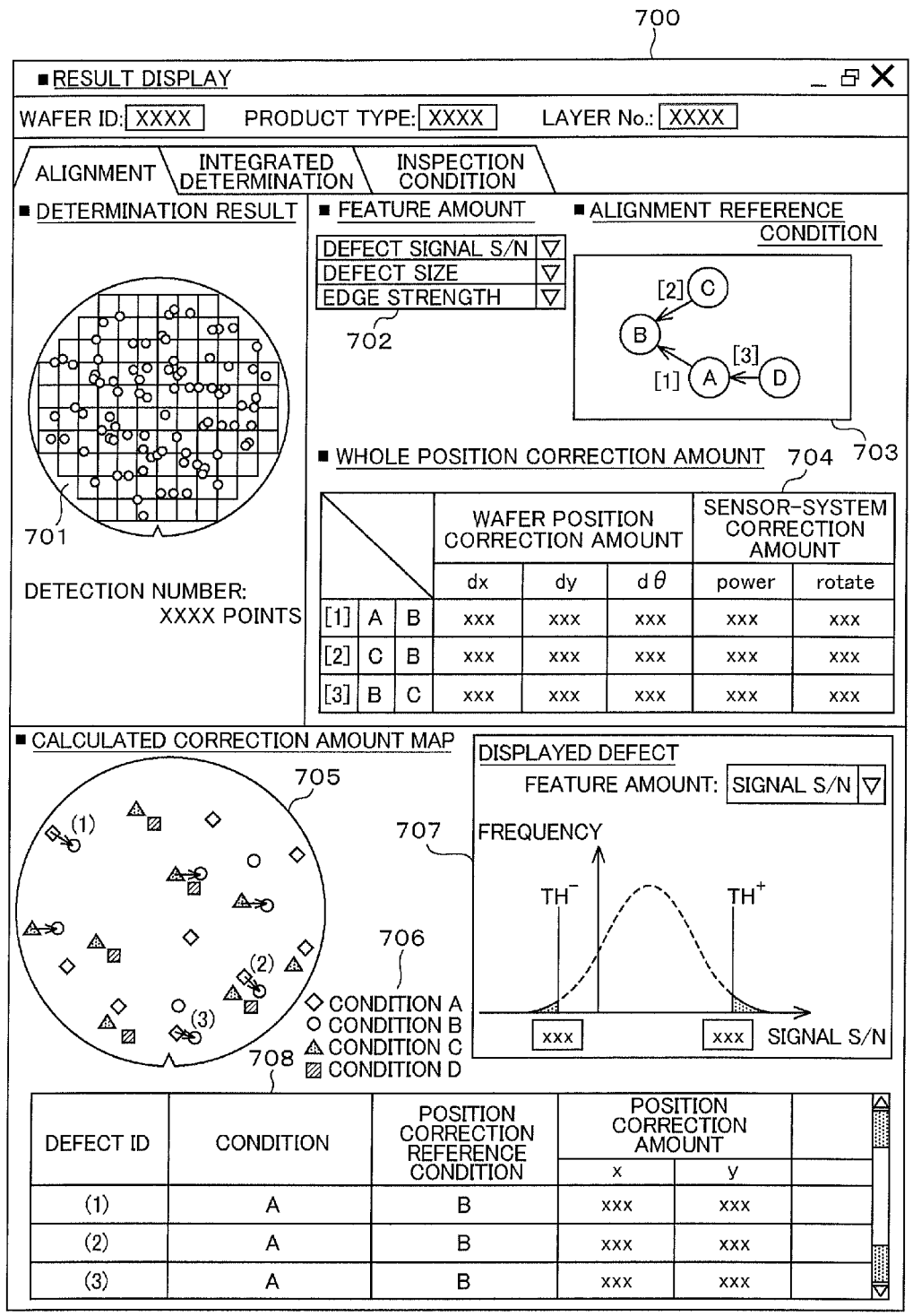
FIG. 9 is a front view of a screen showing an exemplary user interface in the defect inspection device according to the first embodiment of the present invention.

FIG. 9 is a diagram showing an exemplary user interface 700 of the defect inspection device according to this embodiment. A user can confirm the defect determined by the integrated defect determining unit 130 in a wafer map 701. Moreover, the user can also confirm in a display 703 the feature amount used for alignment and the relation of each condition and the alignment reference condition therefor. The position correction amounts 704 of the whole wafer and the local deviation amounts can be displayed. In the display 703, it is specified in which procedure data detected under four conditions A to D are matched as shown as [1], [2], and [3]. Those [1], [2], and [3] correspond to [1], [2], and [3] displayed in a column of the whole position correction amount 704.

Moreover, the state of position correction of the defect candidate on the wafer can be confirmed. A wafer map 705 is a calculated correction amount map which displays the result of calculation of the correction amount for correction under the alignment reference condition in 703 for the defect having the feature amount selected from the feature amounts displayed in 702, in a display form changed for each condition shown in 706. 707 denotes a graph showing the distribution of the feature amounts of the defects having the feature amounts specified in the feature amount display column of 702. The correction amount calculated for the defect detected by using threshold values (TH$^-$, TH$^+$) set on this graph is displayed on the map 705. Table 708 shows, for each defect corresponding to defects (1) to (3) displayed on the calculated correction amount map 705, the result of calculation of the position correction amount for matching data detected under a condition A with a condition B while assuming the condition B as a reference.

Second Embodiment

The second embodiment of the defect inspection method and the defect inspection device of the present invention are described below, using FIGS. 10 to 14.

Figure 10:
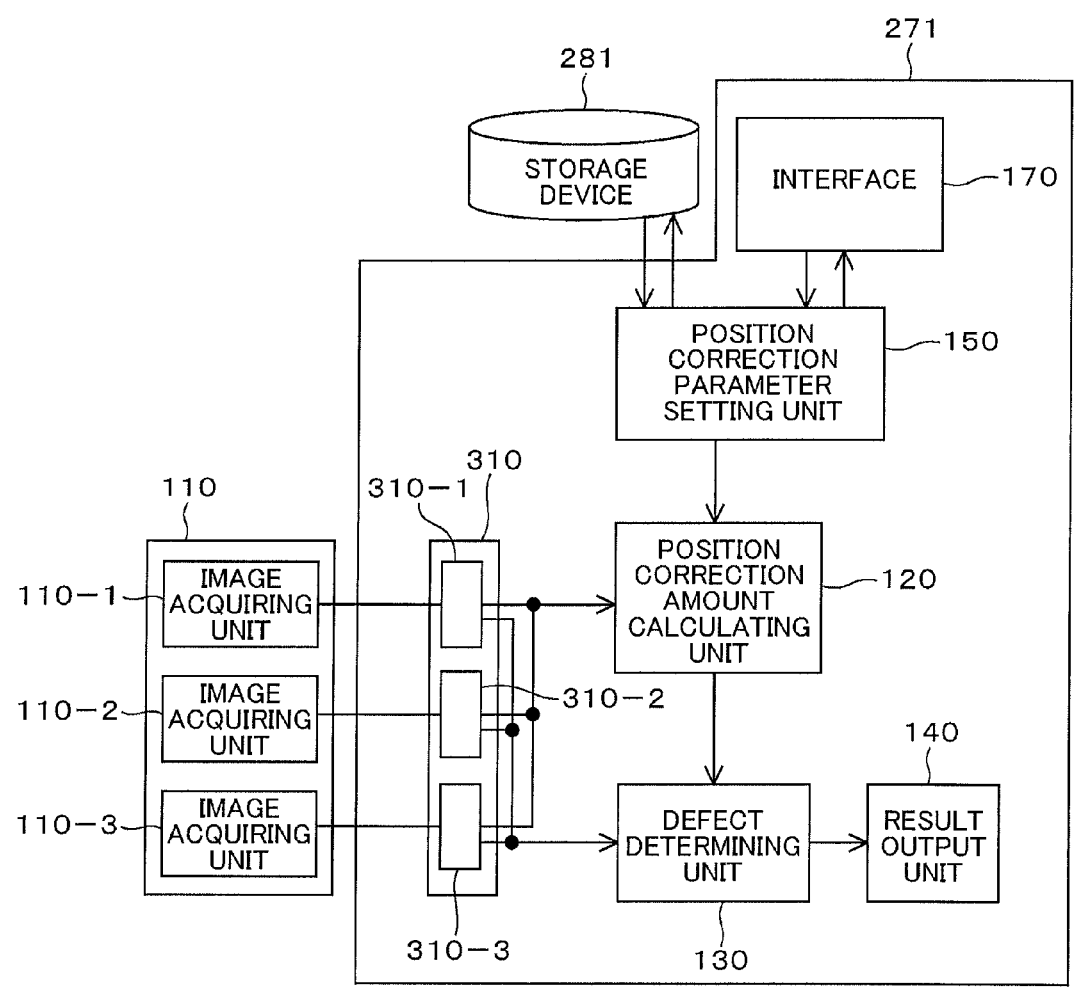
FIG. 10 is a block diagram showing a schematic structure of a defect inspection device according to a second embodiment of the present invention.

FIG. 10 shows an exemplary structure of the defect inspection device of the second embodiment. The defect inspection device according to the second embodiment corresponds to the device in which the image processor and controller unit 270 and the storage device 280 in the defect inspection device described referring to FIG. 2 in the first embodiment are replaced by an image processor and controller unit 271 and a storage device 281 shown in FIG. 10. The image processor and controller unit 271 in this embodiment is configured to include the position correction amount calculating unit 120, the defect determining unit 130, the result output unit 140, a position correction parameter setting unit 150, and an interface 170.

As in the first embodiment, the image acquiring unit 110 shown in FIG. 10 performs image capturing for a sample under a plurality of imaging conditions. The acquired signals are input to the preprocessing unit 310 of the image processor and controller unit 271, where images are created and are subjected to shading correction and dark level correction. Then, the images are sent to the position correction amount calculating unit 120 and the defect determining unit 130 to be processed therein.

The position correction amount calculating unit 120 inputs the images of the respective conditions acquired by the image acquiring units 110-1, 110-2, and 110-3 of the image acquiring unit 110 and the position correction parameter calculated by the position correction parameter setting unit 150 thereto, and calculates the position correction amounts. The defect determining unit 130 performs defect determination using the acquired images of the respective conditions subjected to position correction, based on the calculated position correction amounts, and outputs the result to the result output unit 140.

The position correction parameter setting unit 150 receives, from the storage device 281 and the interface 170, image data acquired in advance, design data of a semiconductor wafer, defect review data acquired by an inspection device different from the aforementioned defect inspection device or a defect observation device such as an electron beam defect observation device, or a parameter or defect indication data input by a user, and calculates the position correction parameter. The position correction parameter setting unit 150 outputs as the position correction parameter a combination of the aforementioned features effective to position correction, the aforementioned template location effective to position correction, a combination of the aforementioned reference image and the image to be corrected, or the like to the position correction amount calculating unit 120.

Figure 11:
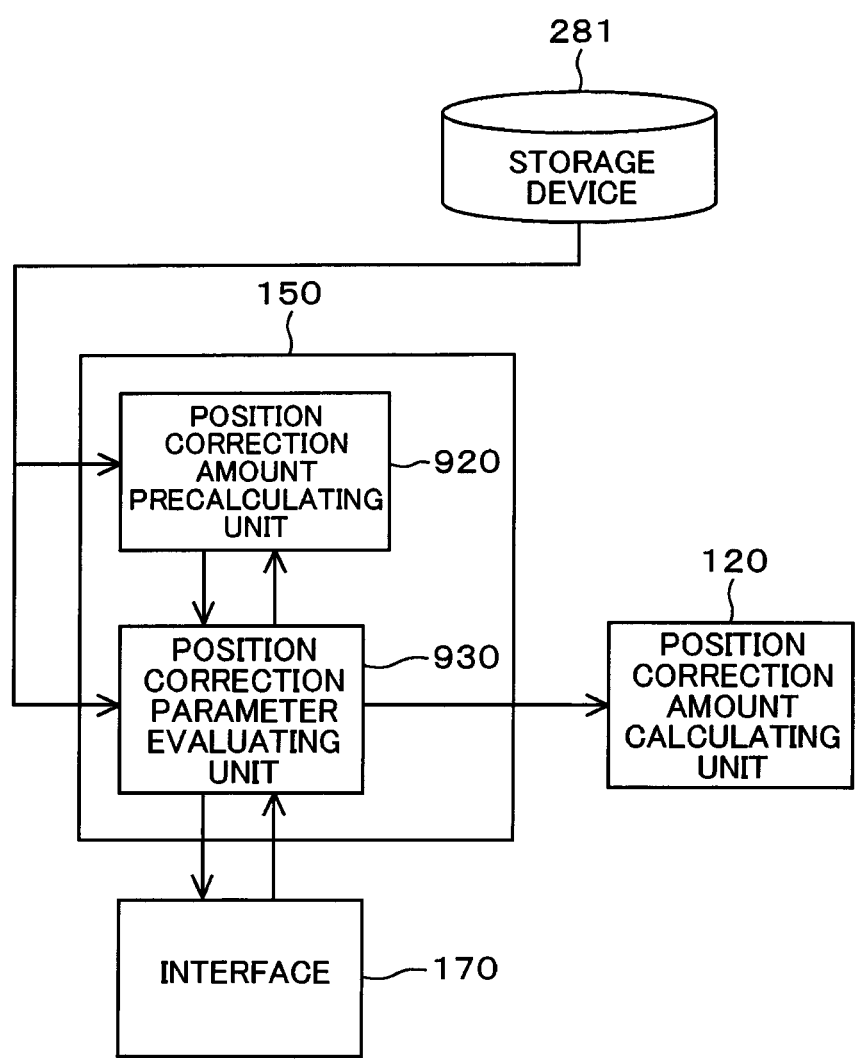
FIG. 11 is a block diagram showing a structure of a position correction parameter setting unit in the defect inspection device according to the second embodiment of the present invention.

FIG. 11 is a diagram showing an exemplary structure of the position correction parameter setting unit 150. As an example of the position correction parameter setting unit 150, the structure for calculating the position correction parameter by using images of a plurality of conditions acquired in advance is shown. Each preprocessing unit 310-1, 310-2, or 310-3 of the preprocessing unit 310 creates image data from the signal obtained by imaging a sample 210 by means of the corresponding image acquiring unit 110-1, 110-2, or 110-3 of the image acquiring unit 110, performs shading correction and dark level correction for the image, data, for example, and stores the processed image data in the storage device 281. In the preprocessing unit 310, it is possible to create an image from the signal obtained by imaging a sample by means of the image acquiring unit 110, extract a feature amount such as the signal strength or the ratio of the signal strength to the background noise (SNR), for the created image data, calculate an outlier, and extract a defect candidate.

The position correction parameter setting unit 150 includes a position correction amount precalculating unit 920 and a position correction parameter evaluating unit 930.

The position correction amount precalculating unit 920 reads image data of a plurality of conditions stored in the storage device 281, and calculates the position correction amounts with at least one position correction parameter which is preset. The position correction parameter evaluating unit 930 receives a set of the position correction parameter and the calculated position correction amounts from the position correction amount precalculating unit 920 and review data from the interface 170, and calculates evaluation values of the position correction amounts calculated by the position correction amount precalculating unit 920. The position correction parameter evaluating unit 930 selects one of a plurality of position correction parameters, which allows position correction with the highest precision to be performed, based on the evaluation values.

The evaluation value of the position correction amount may be the sum of position correction errors of the same defect between the images of the respective conditions. Moreover, a defect determination feature amount may be extracted from images of a plurality of conditions as in the first embodiment, and after calculation of an outlier, the evaluation value of position correction may be calculated based on the separation degree between the defect that the user wants to detect and another defect. The determination of the identity of defect between the images of the respective conditions and the determination whether or not a defect is the defect that the user wants to detect may use defect review data by a defect observation device or a suggestion by the user.

Moreover, the position correction amount precalculating unit 920 can set again at least one position correction parameter based on the position correction parameter selected by the position correction parameter evaluating unit 930. By repeating calculation of the position correction amounts and parameter evaluation by means of the position correction amount precalculating unit 920 and the position correction parameter evaluating unit 930, it is possible to select the position correction parameter which enables the position correction amount calculation to be performed with higher precision. The position correction parameter evaluating unit 930 outputs a combination of the aforementioned features which is effective to position correction, the aforementioned template location effective to position correction, or the aforementioned reference image, for example, to the position correction amount calculating unit 120 as the position correction parameter.

The position correction parameter setting unit 150 can also output the prior position correction amount calculated by the position correction amount precalculating unit 920 to the position correction amount calculating unit 120, and the position correction amount calculating unit 120 can perform position correction based on the prior position correction amount. The calculation of the prior position correction amount may be performed by using a wafer for calculation of prior position correction or a wafer to be inspected. At this stage, it is also possible to correct a magnification error of a sensor and a static position deviation such as a deviation of the sensor attached position among the prior position correction amounts.

Figure 12:
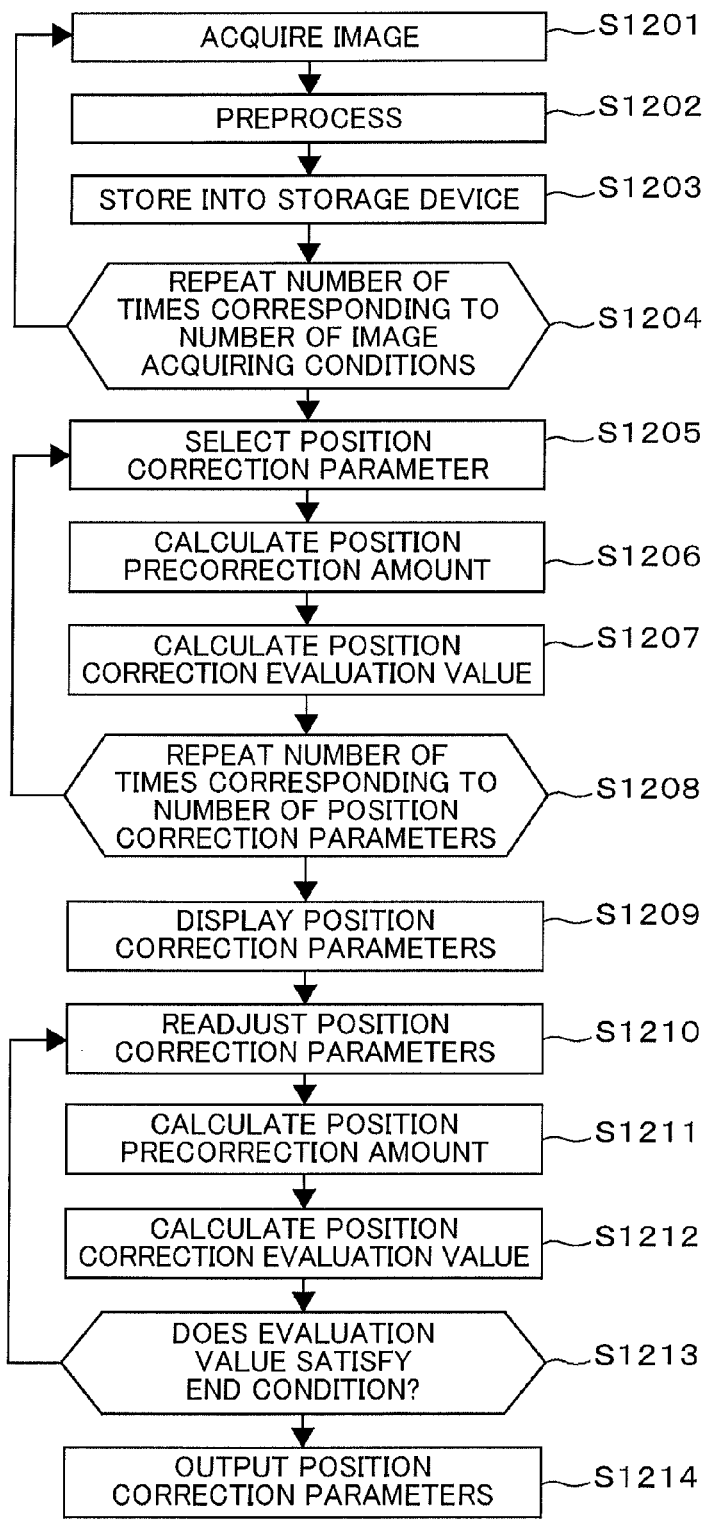
FIG. 12 is a flowchart showing a flow of processing for position correction parameter setting in the defect inspection method according to the second embodiment of the present invention.

FIG. 12 is a diagram showing an exemplary procedure for setting the position correction parameter of the defect inspection device according to this embodiment. First, a sample 210 that is an inspection object is imaged by using a plurality of image acquiring units 110-1 to 110-3 of the image acquiring unit 110 (S1201). The signals obtained by the imaging are input to the image processor and controller unit 271, and images are created and subjected to preprocessing, e.g., shading correction and dark level correction, in the preprocessing unit 310 (S1202). The preprocessed images are stored in the storage device 281 (S1203). S1201 to S1203 are repeated the number of times which corresponds to the number of the image acquiring conditions (S1204). Then, a predetermined position correction parameter is selected (S1205). The image data stored in the storage device 281 is input to the position correction parameter setting unit 150, and the prior position correction amount is calculated by the position correction amount precalculating unit 920, using the position correction parameter selected in S1205 (S1206). Based on the calculated prior position correction amount, the evaluation value of position correction is calculated in the position correction parameter evaluating unit 930 (S1207). S1205 to S1207 are repeated the number of times which corresponds to the number of position correction parameters (S1208).

Then, the position correction parameter obtained in S1205 to S1208 is displayed on the screen of the interface 170 (S1209), and readjustment of the position correction parameter is performed on the screen of the interface 170 (S1210). This readjustment may be performed by modifying the correction parameter displayed on the screen by an operator, or may be automatically performed. Based on the readjusted position correction parameter, the prior position correction amount is calculated in the position correction amount precalculating unit 920 (S1211), and the position correction evaluation value is calculated in the position correction parameter evaluating unit 930 (S1212). Until the position correction evaluation value calculated in S1212 satisfies an end condition, readjustment of the position correction parameter is repeated (S1213). Finally, the position correction parameter satisfying the condition is output (S1214).

In the calculation of the position correction amount evaluation value (S1207), the evaluation value can be calculated using a suggestion by a user or defect review data by a defect observation device. Among the position correction parameters calculated in S1205 to S1208, one providing the best position correction evaluation value may be determined as a final position correction parameter.

The steps from the position correction between a plurality of images using the thus determined position correction parameter, through calculation of the defect determination feature amount and outlier extraction, to the output of the result are the same as those from S805 to S808 described referring to FIG. 8 in the first embodiment, and therefore the description is omitted.

Figure 13:
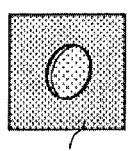
FIG. 13 is a front view of a screen of a user interface related to the position correction parameter setting in the defect inspection device according to the second embodiment of the present invention.

FIG. 13 is a diagram showing an exemplary user interface 1100 displayed on the screen of the interface 170 in relation to the position correction parameter setting in the defect inspection device according to this embodiment. The user can choose whether or not to set a position correction parameter for each condition as an object of position correction (object condition D in the example shown in FIG. 13) and the condition as the object of position correction, by means of a condition-based parameter setting unit 1101.

In an evaluation result displaying unit 1102, an evaluation value based on the aforementioned selected defect deviation amount for each position correction parameter or an evaluation value based on the separation degree of the selected defect is displayed, and the content of the correction parameter at that time is displayed. The user can choose a parameter to be used for position correction, from a set of a plurality of position correction parameters. It is possible to manually adjust the set of position correction parameters by clicking a parameter set adjustment button 1103 on the screen, or to automatically select the most appropriate parameter set by clicking the parameter set adjustment button 1104 on the screen.

In a defect review screen display region 1105, an SEM image 1105-1 and an optical microscope image 1105-2 of a reviewed defect acquired from the defect observation device are displayed. The user can confirm the aforementioned image data of each condition of the reviewed defect in a display region 1105-3, and can manually set the defect position in the image from a coordinate specifying region 1105-4.

Moreover, in a position correction object condition setting region 1106, a combination of the condition as the object of position correction 1106 and a reference condition of position correction 1107 can be confirmed. Furthermore, from the condition as the object of position correction 1106, it is possible to confirm the scanning direction, the illumination condition, the detection condition, or the like in each condition. Based on this, the user can also edit the combination of the position correction reference conditions 1107.

Figure 14:
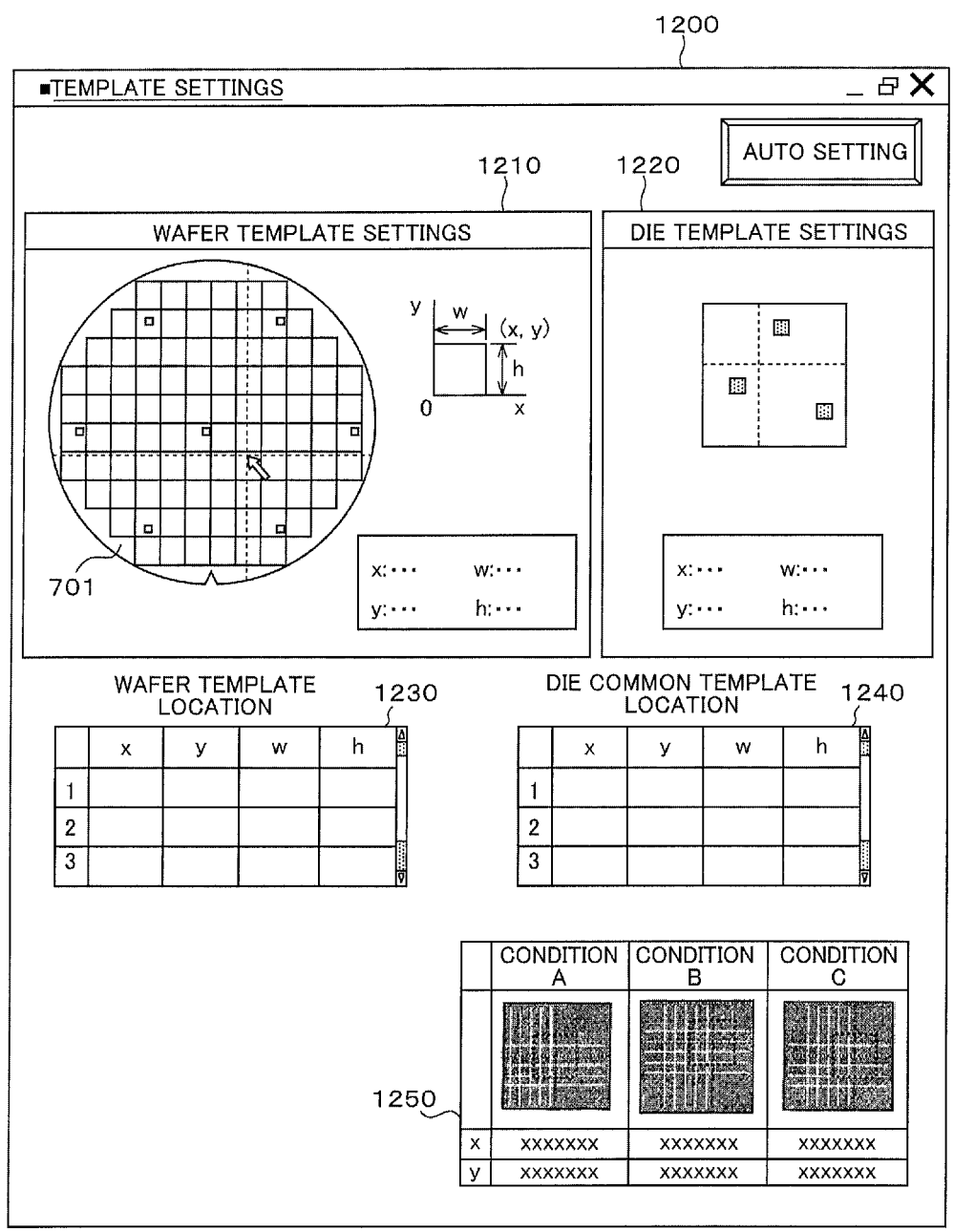
FIG. 14 is a front view of a screen of a user interface related to template setting in the defect inspection device according to the second embodiment of the present invention.

FIG. 14 is a diagram showing an exemplary user interface 1200 related to the template setting in the defect inspection device according to this embodiment. In the user interface 1200, a wafer template setting region 1210, a die template setting region 1220, a wafer template location setting region 1230, a die common template location setting region 1240, and a review image display region 1250 are displayed. The user directly specifies a position by a coordinate in the wafer template setting region 1210 or the die template setting region 1220, thereby being able to set the template location in the wafer template location setting region 1230 or in the die common template location setting region 1240. Also, the user can directly confirm image data in a specified region on the wafer template setting region 1210 or the die template setting region 1220 by displaying the image data in the review image display region 1250, and can specify the template in the wafer template location setting region 1230 or the die common template location setting region 1240. The template may be set at a given location on the wafer or at a given location in the die.

Third Embodiment

The third embodiment of the defect inspection technique (the defect inspection method and the defect inspection device) of the present invention is described below, referring to FIGS. 15 and 16. In this embodiment, an image of a defect candidate is extracted first from an image obtained by imaging a sample to be inspected, and the extracted image of the defect candidate is processed so that a defect is extracted, thereby the transfer amount of image data is reduced and the device structure can be simplified as compared with those in the first and second embodiments.

Figure 15:
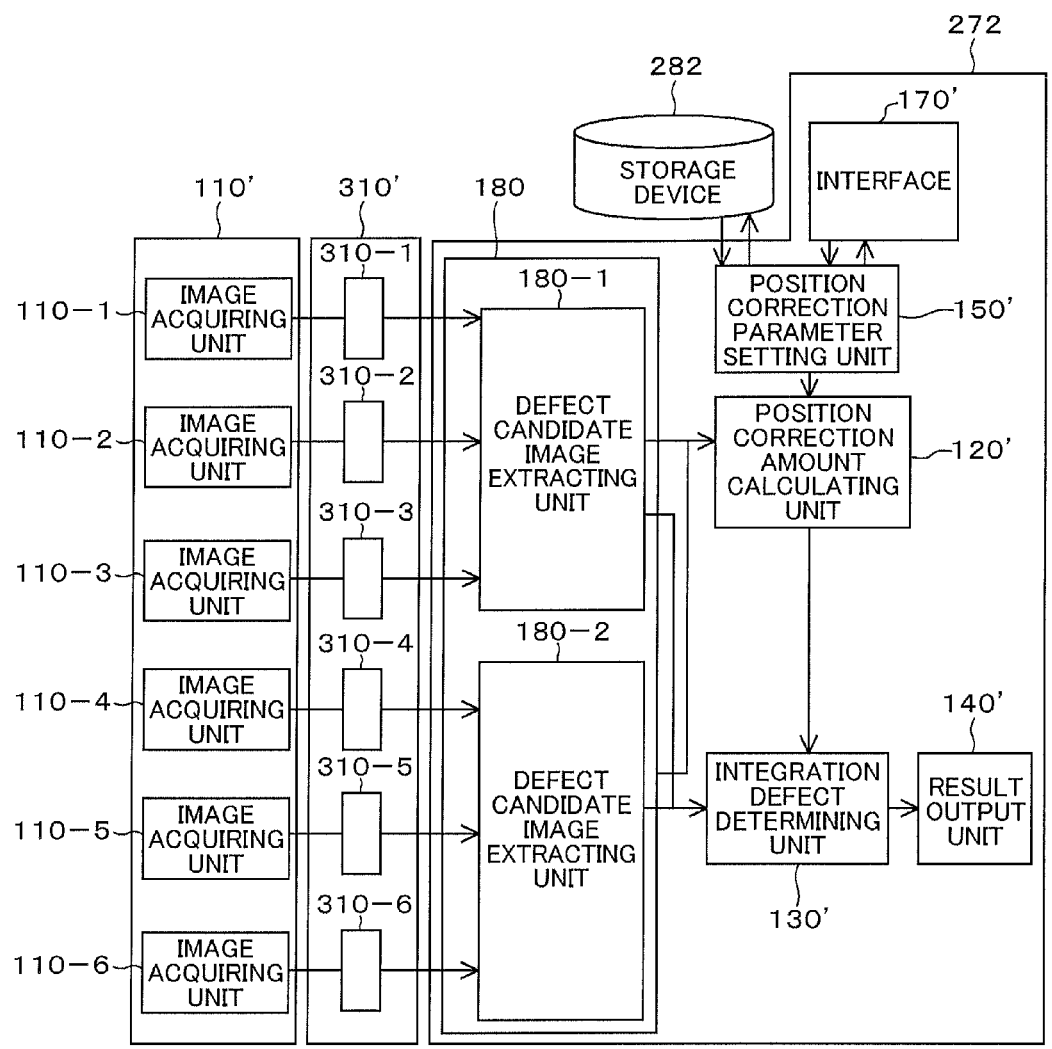
FIG. 15 is a block diagram showing a schematic structure of a defect inspection device according to a third embodiment of the present invention.

FIG. 15 shows an exemplary structure of the defect inspection device according to the third embodiment. The defect inspection device according to this embodiment is configured to include an image acquiring unit 110', a preprocessing unit 310', a defect candidate image extracting unit 180, a position correction amount calculating unit 120', an integrated defect determining unit 130', a result output unit 140', and a position correction parameter setting unit 150'. The image acquiring unit 110' includes image acquiring units 310'-1 to 310'-6, performs image-capturing of a sample under a plurality of imaging conditions as in the first embodiment, and outputs acquired image data to the defect candidate image extracting unit 180. Note that the image acquiring unit 110', the preprocessing unit 310', the position correction amount calculating unit 120', the integrated defect determining unit 130', the result output unit 140', and the position correction parameter setting unit 150', and the interface 170' are labeled with ', these are basically the same in structure as those described in the first or second embodiment. These are labeled with' because data handled by these is different.

The defect candidate image extracting unit 180 includes defect candidate image extracting units 180-1 and 180-2, extracts an image containing a defect candidate from the image of each condition acquired by the image acquiring unit 110', and transfers the extracted image to the position correction amount calculating unit 120' and the integrated defect determining unit 130'. From the image extracting unit 180-1, extraction is performed from image data acquired by the image acquiring units 110-1, 110-2, and 110-3 of the image acquiring unit 110'. In the defect candidate image extracting unit 180-2, extraction is performed from image data acquired by the image acquiring units 110-4, 110-5, and 110-6 of the image acquiring unit 110'. Although the structure in which the defect candidate image extracting unit 180 includes two image extracting units 180-1 and 180-2 in this example, it is enough that any one of at least one image acquiring units 110-1 to 110-6 is connected to at least one defect candidate image extracting unit 180-1 or 180-2.

In the position correction amount calculating unit 120', the image extracted in the defect candidate image extracting unit 180 and a position correction parameter calculated by the position correction parameter setting unit 150' are input. The position correction amount calculating unit 120' calculates the position correction amount, and outputs it to the integrated defect determining unit 130'. The integrated defect determining unit 130' performs position correction of each condition image based on the calculated position correction amount, performs defect determination using the acquired image of each condition, after being subjected to position correction, and then outputs the result to the result output unit 140'.

Figure 16:
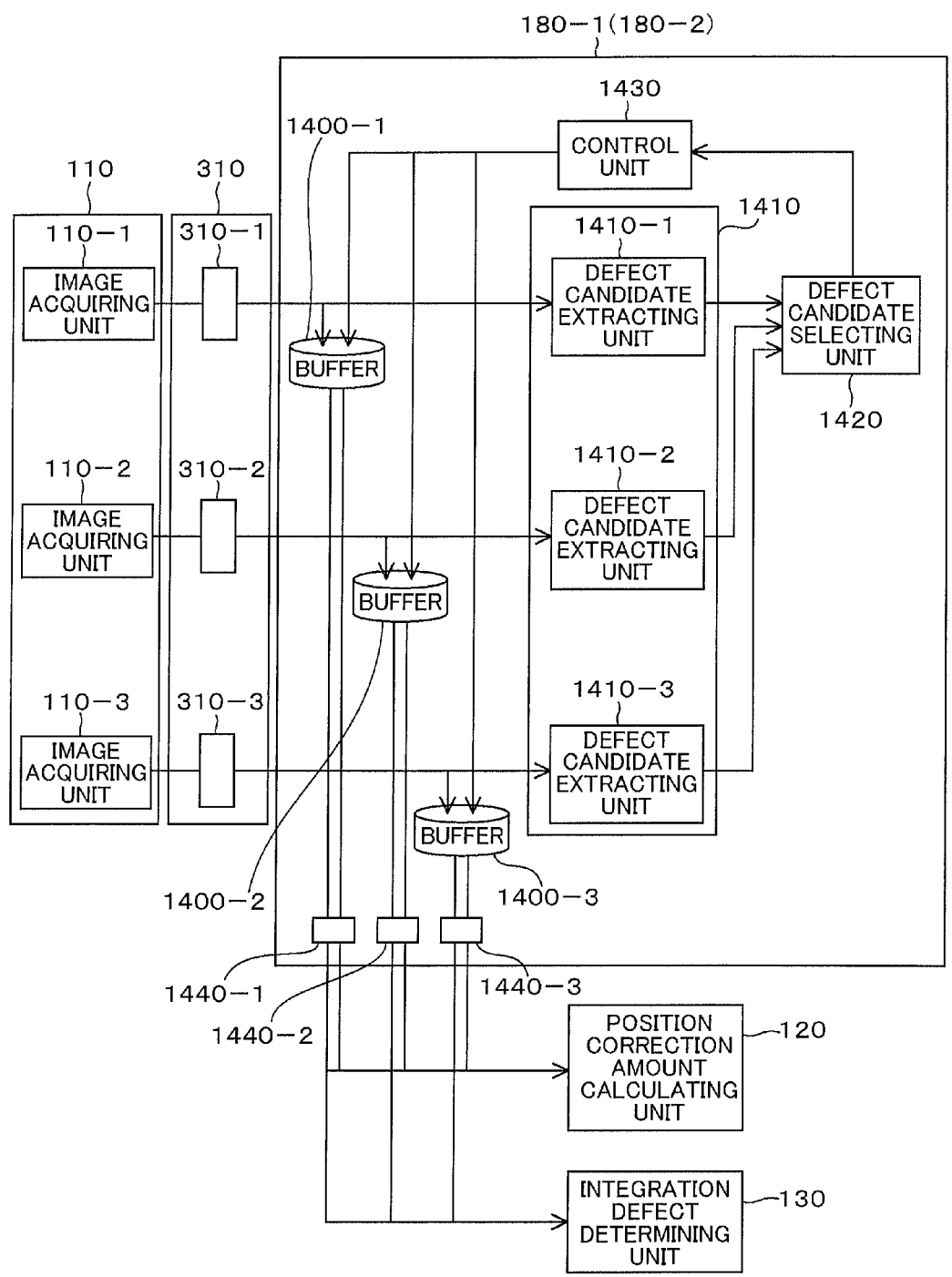
FIG. 16 is a block diagram showing a structure for extraction of a defect candidate image in the defect inspection device according to the third embodiment of the present invention.

FIG. 16 shows an exemplary structure of the defect candidate image extracting unit 180-1 of the defect candidate image extracting unit 180 in this embodiment. The defect candidate image extracting unit 180-1 is configured to include image storing buffers 1400-1 to 1400-3, defect candidate extracting units 1410-1 to 1410-3, a defect candidate selecting unit 1420, and a control unit 1430. The defect candidate image extracting unit 180-2 is similarly configured. The image acquiring unit 110' images a sample to be inspected and outputs signals. The signals output from the image acquiring unit 110' are input to the preprocessing unit, so that images are created. The thus created data of images are transferred to the image storing buffers 1400 and the defect candidate extracting unit 1410.

The defect candidate extracting unit 1410 extracts a feature amount such as an image brightness difference between a detection die and its adjacent die for every pixel of the image data, or the sum or the variation of the brightness difference in a region of fixed size, forms a feature amount space from the aforementioned feature amounts, and extracts an outlier in the feature amount space as a defect candidate. As the reference for determining the outlier, the variation of data points in the feature amount space or the distance of a data point from the center of gravity can be used, for example. The information on the signal strength or the coordinate of the extracted defect candidate, for example, is transferred to the defect candidate selecting unit 1420. The defect candidate selecting unit 1420 removes false information that is erroneous detection of a noise or the like, and a nuisance that a user does not want to detect, from the defect candidate and sends the information on the remaining defect candidate to the control unit 1430.

The coordinate of the defect candidate is sent from the control unit 1430 to the image storing buffers 1400-1 to 1400-3, images containing the defect candidate are extracted from the image data output from the preprocessing units 310-1 to 310-3 and stored in the image storing buffers 1400-1 to 1400-3, by the image extracting units 1440-1 to 1440-3, and the extracted images are transferred to the position correction amount calculating unit 120' and the integrated defect determining unit 130'. The processes in the position correction amount calculating unit 120' and the integrated defect determining unit 130' are the same as those in the position correction amount calculating unit 120' and the integrated defect determining unit 130' described in the first or second embodiment, and therefore the description thereof is omitted.

In this embodiment, an exemplary structure in which extraction of a defect candidate image is performed prior to integrated defect determination is described. This structure enables reduction of the image data transfer amount, as compared with the structure of the first or second embodiment in which integrated defect determination is performed by the image data. Furthermore, since it is enough that position correction is performed only for the defect candidate, integrated defect determination can be achieved at a high speed.

The present invention is not limited to the above embodiments, but may contain various modifications. For example, the aforementioned embodiments are described in detail for the sake of easy-to-understand explanation of the present invention, but the present invention is not always limited to include all the described components. Moreover, a portion of the structure of one embodiment can be replaced by the structure of another embodiment. Also, the structure of one embodiment can be added to the structure of another embodiment. Furthermore, for a portion of the structure of each embodiment, addition, deletion, or replacement of another structure can be made.

In addition, the respective structures, functions, processing units, processing means, and the like described above may be entirely or partly implemented by hardware, for example, by being designed with an integrated circuit. Also, the respective structures, functions and the like described above may be implemented by software, for example, by interpretation and execution of programs for achieving the respective functions by means of a processor. Information such as a program, a table, a file, and the like for achieving each function can be stored in a storage device such as a memory, a hard disk, or a SSD (Solid State Drive) or a recording medium such as an IC card, an SD card, or DVD.

For the control lines and the information lines, those considered to be necessary for the description are shown, but all control lines and information lines on a product are not necessarily shown. Actually, it can be considered that almost all the structures are mutually connected.

LIST OF REFERENCE SIGNS

110 . . . image acquiring unit, 120 . . . position correction amount calculating unit, 130 . . . integrated defect determining unit, 140 . . . result output unit, 150 . . . position correction parameter setting unit, 160 . . . storage device, 170 . . . interface, 180 . . . defect candidate image extracting unit, 210 . . . wafer, 220 . . . stage, 230 . . . controller, 240 . . . illumination system, 250 . . . detector system, 260 . . . image sensor, 270 . . . controller, 280 . . . storage device, 310 . . . preprocessing unit, 320 . . . feature amount calculating unit, 330 . . . position correction amount determining unit, 340 . . . storage device, 610 . . . position correcting unit, 620 . . . defect determination feature amount calculating unit, 630 . . . outlier calculating unit, 910 . . . preprocessing unit, 920 . . . position correction amount precalculating unit, 930 . . . position correction parameter evaluating unit, 1400 . . . buffer, 1410 . . . defect candidate extracting unit, 1420 . . . defect candidate selecting unit, 1430 . . . control unit

The invention claimed is:

1. A defect inspection method comprising:
   irradiating illumination light onto a sample;
   detecting a plurality of images having different imaging conditions based on scattered light emitted from the sample by the irradiated illumination light;
   extracting feature data based on the detected plurality of images having different imaging conditions, the feature data being at least one of a feature amount image having one or more values for each pixel constituting the detected plurality of images, a feature point having information on a coordinate on the sample, and a weighed feature point at which the respective feature points each have a feature amount of a real value or an attribute of a discrete value based on a histogram which includes a frequency of each respective feature amount;
   calculating a plurality of position correction amounts for the detected plurality of images by comparing the extracted feature data of an image of a preset reference condition, using at least one position correction template, from among the detected plurality of images having different imaging conditions, with the extracted feature data of the remaining images from the detected plurality of images, other than the image of the preset reference condition;
   correcting positions of the plurality of images based on the calculated position correction amounts;
   extracting a defect candidate based on the corrected plurality of images; and
   calculating a correction amount wafer map which indicates position correction amounts for an alignment reference condition for a defect having one feature amount selected from a plurality of feature amounts,
   wherein said different imaging conditions comprise at least two different image resolutions, and
   wherein said calculating a plurality of position correction amounts comprises calculating a first position correction amount and thereafter calculating a second position correction amount, said first position correction amount being calculated using an edge corner feature, and said second position correction amount providing fine alignment calculated using a signal strength feature.

2. The defect inspection method according to claim 1, wherein the feature amount image whose feature data is extracted is a feature amount image acquired by extracting an edge strength of a background pattern as the feature amount; the feature points correspond to a distribution of feature points acquired by quantizing the feature amount image; and the weighed feature points are acquired by giving the feature amounts to the respective feature points in the feature amount image.

3. The defect inspection method according to claim 1, wherein the image of the reference condition is determined based on one of a direction of a wiring pattern on the sample, a polarization state of the illumination light at the irradiating step, and a direction in which the sample is scanned.

4. A defect inspection device comprising:
an illumination light source configured to irradiate illumination light onto a sample; and
a processor configured to:
detect a plurality of images having different imaging conditions based on scattered light emitted from the sample by the irradiated illumination light;
extract feature data based on the detected plurality of images having different imaging conditions, the feature data being at least one of a feature amount image having one or more values for each pixel constituting the detected plurality of images, a feature point having information on a coordinate on the sample, and a weighed feature point at which the respective feature points each have a feature amount of a real value or an attribute of a discrete value based on a histogram which includes a frequency of each respective feature amount;
calculate a plurality of position correction amounts for the detected plurality of images by comparing the extracted feature data of an image of a preset reference condition, using at least one position correction template, from among the detected plurality of images having different imaging conditions, with the extracted feature data of the remaining images from the detected plurality of images, other than the image of the preset reference condition;
correct positions of the plurality of images based on the calculated position correction amounts;
extract a defect candidate based on the corrected plurality of images; and
calculate a correction amount wafer map which indicates position correction amounts for an alignment reference condition for a defect having one feature amount selected from a plurality of feature amounts,
wherein said different imaging conditions comprise at least two different image resolutions, and
wherein said calculating of a plurality of position correction amounts comprises calculating a first position correction amount and thereafter calculating a second position correction amount, said first position correction amount being calculated using an edge corner feature, and said second position correction amount providing fine alignment calculated using a signal strength feature.

5. The defect inspection device according to claim 4, wherein the feature amount image is a feature amount image acquired by extracting an edge strength of a background pattern as the feature amount; the feature points correspond to a distribution of feature points acquired by quantizing the feature amount image; and the weighed feature points are acquired by giving the feature amounts to the respective feature points in the feature amount image.

6. The defect inspection device according to claim 4, wherein the image of the reference condition is determined based on one of a direction of a wiring pattern on the sample, a polarization state of the illumination light, and a direction in which the sample is scanned.

* * * * *